United States Patent
Vogt et al.

(10) Patent No.: US 9,078,959 B2
(45) Date of Patent: Jul. 14, 2015

(54) COATING METHOD AND COATING DEVICE

(75) Inventors: Sebastian Vogt, Erfurt (DE); Klaus-Dieter Kühn, Marburg-Elnhausen (DE)

(73) Assignee: Heraeus Medical GmbH, Wehrheim (DE)

( * ) Notice: Subject to any disclaimer, the term of this patent is extended or adjusted under 35 U.S.C. 154(b) by 314 days.

(21) Appl. No.: 13/330,936

(22) Filed: Dec. 20, 2011

(65) Prior Publication Data

US 2012/0164309 A1 Jun. 28, 2012

Related U.S. Application Data

(60) Provisional application No. 61/432,678, filed on Jan. 14, 2011.

(30) Foreign Application Priority Data

Dec. 23, 2010 (DE) .......................... 10 2010 055 559

(51) Int. Cl.
| | |
|---|---|
| B05C 11/00 | (2006.01) |
| A61L 31/16 | (2006.01) |
| A61L 27/30 | (2006.01) |
| A61L 27/32 | (2006.01) |
| A61L 27/54 | (2006.01) |
| A61L 31/08 | (2006.01) |

(52) U.S. Cl.
CPC ............... *A61L 31/16* (2013.01); *A61L 27/306* (2013.01); *A61L 27/32* (2013.01); *A61L 27/54* (2013.01); *A61L 31/086* (2013.01); *A61L 31/088* (2013.01); *A61L 2300/60* (2013.01); *A61L 2430/24* (2013.01)

(58) Field of Classification Search
CPC ....................................................... B05C 17/00
USPC ................................... 132/73.5, 73; 118/270
See application file for complete search history.

(56) References Cited

U.S. PATENT DOCUMENTS

| | | | | |
|---|---|---|---|---|
| 4,282,891 | A | * | 8/1981 | Duceppe ...................... 132/73.5 |
| 5,607,685 | A | | 3/1997 | Cimbollek et al. |
| 5,679,646 | A | | 10/1997 | Cimbollek et al. |
| 7,030,093 | B2 | | 4/2006 | Vogt et al. |
| 7,563,324 | B1 | | 7/2009 | Chen et al. |

(Continued)

FOREIGN PATENT DOCUMENTS

| | | |
|---|---|---|
| DE | 4404018 A1 | 8/1995 |
| DE | 10142465 A1 | 7/2003 |

(Continued)

OTHER PUBLICATIONS

English translation of an Office Action issued Oct. 29, 2013 in CN Application No. 201110437701.8.

(Continued)

*Primary Examiner* — Dah-Wei D Yuan
*Assistant Examiner* — Andrew Bowman
(74) *Attorney, Agent, or Firm* — Panitch Schwarze Belisario & Nadel LLP

(57) ABSTRACT

A device for coating at least regions of a medical implant includes an elastically deformable transfer means having a liquid that contains at least one pharmaceutically active substance. The liquid can be transferred to the medical implant when the transfer means is contacted with a surface of the medical implant.

8 Claims, 2 Drawing Sheets

(56) References Cited

U.S. PATENT DOCUMENTS

| | | |
|---|---|---|
| 2004/0062592 A1 | 4/2004 | Shekalim et al. |
| 2005/0031664 A1 | 2/2005 | Vogt et al. |
| 2005/0074544 A1 | 4/2005 | Pacetti et al. |
| 2006/0029722 A1 | 2/2006 | Larson et al. |
| 2007/0125247 A1 | 6/2007 | Kunstmann et al. |
| 2007/0281072 A1 | 12/2007 | O'Connor et al. |
| 2008/0206442 A1 | 8/2008 | Shekalim et al. |

FOREIGN PATENT DOCUMENTS

| | | |
|---|---|---|
| DE | 10351150 A1 | 5/2005 |
| EP | 0623349 A1 | 11/1994 |
| EP | 1374923 A2 | 1/2004 |
| EP | 1470829 A1 | 10/2004 |
| WO | 2005037447 A1 | 4/2005 |
| WO | 2005042045 A1 | 5/2005 |
| WO | 2007050565 A2 | 5/2007 |
| ZA | 200206983 A | 5/2003 |

OTHER PUBLICATIONS

Search Report issued Apr. 25, 2012 in EP Application No. 11009580.9.

Office Action issued Feb. 7, 2013 in AU Application No. 2011265337.

Office Action issued Mar. 28, 2013 in CA Application No. 2,760,893.

Office Action issued Jul. 5, 2011 in DE Application No. 10 2010 055 559.2.

Office Action issued Feb. 5, 2014 in DE Application No. 10 2010 055 559.2.

* cited by examiner

COATING METHOD AND COATING DEVICE

CROSS-REFERENCE TO RELATED APPLICATIONS

The present application claims priority to U.S. Provisional Patent Application No. 61/432,678, entitled "Coating Process and Coating Apparatus" and filed Jan. 14, 2011.

BACKGROUND OF THE INVENTION

The present invention relates generally to a method for coating, at least regions of, a medical implant, preferably of an artificial joint or a fixation for a joint.

The present invention also relates generally to a device for coating, at least regions of, a medical implant using said method.

The coating of medical implants with pharmaceutical agents has garnered increasing attention in recent years. Antibiotic protection of the surface of implant materials is a main application of coating methods in this context.

Any implantation of articular endoprostheses, and of osteosynthesis materials as well, is associated with a certain risk of microbial contamination. Successful colonization of microbial pathogens on the surface of the implant can lead to the manifestation of post-operative osteitis/osteomyelitis. Osteitis/osteomyelitis is a severe complication for the patient and, in addition, associated with substantial costs.

Gentamicin-doped PMMA bone cement has been in clinical use with cemented articular endoprostheses for decades with much success. The broadband antibiotic, gentamicin, contained in the bone cement protects the surface of the bone cement effectively from bacterial infections.

With regard to non-cemented articular endoprostheses and osteosynthesis materials, a number of approaches has been proposed in order to also attain local antibiotic protection of the implant surfaces.

For example, the use of poorly water-soluble antibiotic salts has been described in several patent documents. For exemplary purposes, EP 0 623 349 A1, EP 1 470 829 A1, EP 1 374 923 A2, DE 101 42 465 A1, and DE 44 04 018 A1 can be cited in this context. The poorly water-soluble salts dissolve while releasing the antibiotics contained therein as a result of the action of body fluids. Prolonged release of the agent is advantageous. However, the laborious production of the salts is disadvantageous.

Alternatively, it is feasible to use water-soluble antibiotic salts. This is associated with a problem related to fixation of the antibiotic on the implant surface.

The majority of coatings that have been described thus far is preferably intended for the manufacture of coated implants under industrial conditions. This means that the industrial coating of said implants can only involve few agents that are relevant for large-scale use in order to be able to guarantee that the industrial manufacture is economic through sufficiently large throughput.

In particular in the case of antibiotic coatings, though, considering the increasingly problematic resistance status and the ensuing increased manifestation of multi-resistant pathogens, such as MRSA and MRSE, it is of interest to use antibiotics or combinations of antibiotics, which are specifically adapted to the germ at hand, for the coating of revision prostheses in one-stage or two-stage septic articular endoprosthesis replacement in order to ensure effective initial antibiotic protection of the implant surfaces.

This is disadvantageous in that the methods for coating the medical implants are relatively laborious. Variable short-term application is not feasible. Various scenarios then necessitate the stock-keeping of various coated medical implants in order to meet the needs of the different patients. This requires extensive stock-keeping and prevents uncommon solutions for specific cases.

BRIEF SUMMARY OF THE INVENTION

Accordingly, it is an objective of a preferred embodiment of the present invention to overcome the disadvantages of the prior art. In particular, a simple and easy-to-use method and a device are to be provided for this purpose that can be used to coat a medical prosthesis without interfering with an ongoing surgery (OR). The aim is to be able to coat as many different medical implants as possible using the same method and the same device. Moreover, the method and the device should be variable to use such that they can be adapted to the medical needs, in particular to a suitable medication for the patient. The cleanliness required in operating theatres is another factor to take into account.

It is also an objective of a preferred embodiment of the present invention to develop a coating method that is as simple as possible and can be used by the OR staff during an ongoing surgery, with the least time expenditure, to coat very different implants from any manufacturers with pharmaceutical preparations. Moreover, it is an objective of a preferred embodiment of the present invention to develop a simple coating device that allows the OR staff to coat implants under OR conditions with the least effort possible using any liquid pharmaceutical preparations. Moreover, the device is to be designed such that, to the extent possible, no spray mist or droplets can contaminate the OR area. Another objective is that the device should, in particular, be suitable for the coating of non-cemented articular endoprostheses and osteosynthesis materials.

The objective of a preferred embodiment of the present invention are met in that a medical implant having a surface to be coated is provided and the medical implant surface to be coated is contacted with an elastically deformable transfer means that comprises at least one liquid that contains at least one pharmaceutically active substance, whereby the liquid is transferred from the transfer means to the medical implant surface through the contacting with the transfer means. The contacting preferably proceeds such that the medical implant surface to be coated is pressed against an elastically deformable transfer means that comprises at least one liquid that contains at least one pharmaceutically active substance and/or is swept over an elastically deformable transfer means of the type, whereby the liquid is transferred from the transfer means to the medical implant surface to be coated during the pressing against and/or sweeping over said transfer means.

Methods according to a preferred embodiment of the present invention are carried out before inserting the medical implants. Accordingly, the methods proceed "ex vivo."

According to a preferred embodiment of the present invention, a pharmaceutically active substance shall be understood to mean pharmaceutically effective means or means with a pharmacological effect as well as means that support a pharmacological effect or support in any other way the self-healing forces of the body. Examples include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

The scope of a preferred embodiment of the present invention can also provide that the liquid comprises an aqueous solution of an antibiotic, preferably that an aqueous gentamicin sulfate solution with a gentamicin sulfate content of 10.0 to 88.0% by weight is used, whereby it is particularly preferred to use a gentamicin sulfate solution with a gentamicin sulfate content of 75.0 to 80.0% by weight. The gentamicin sulfate solution has an oily-viscous consistency and adheres very well to metal surfaces.

In this context, a preferred embodiment of the present invention can further provide that common pharmaceutical stabilizers are contained in the gentamicin sulfate solutions. These improve the durability and thus the usability of the liquid to be applied.

A preferred embodiment of the present invention can also provide for the use of other aminoglycoside antibiotic solutions such as aqueous solutions of tobramicin sulfate, amikacin sulfate, netilmicin sulfate, and sisomicin sulfate as liquid or components of the liquid. It is also feasible to use aqueous solutions of vancomycin, dalbavancin, ramoplanin, daptomycin, moxifloxacin, clindamycin, and lincomycin.

Moreover, the scope of a preferred embodiment of the present invention can provide for the use of combinations of solutions of different antibiotics as liquid. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride.

A preferred embodiment of the present invention can further provide for antiseptics solutions to be used as liquid, in particular solutions of chlorohexidine digluconate, octenidine dihydrochloride, and polyhexanide.

The scope of a preferred embodiment of the present invention also includes that the liquid comprises solutions of antibiotics and antiseptic agents that contain, as solvents, organic solvents or combinations of organic solvents or combinations of organic solvents and water. This allows, for example, poorly water-soluble antibiotic salts, such as laurates, myristates, palmitates, and stearates, to be used as well. Moreover, poorly water-soluble antibiotics or antibiotic salts in the form of aqueous suspensions can also be used.

A particularly advantageous refinement of the method according to a preferred embodiment of the present invention provides the liquid to be transferred out of the transfer means onto the medical implant surface to be coated, preferably out of channels, at least one reservoir chamber, pores, fibers and/or intervening spaces of the transfer means.

Moreover, it is a particular advantage for a preferred embodiment of the present invention to provide the liquid to be introduced into the transfer means, preferably into channels, at least one reservoir chamber, pores, fibers and/or intervening spaces of the transfer means or the transfer means to be soaked in the liquid, in particular right before its use. This ensures the variability of the method.

In this context, a preferred embodiment of the present invention can provide a liquid matching the treatment scenario, in particular an antibiotic or mixture of antibiotics matching the treatment scenario, being introduced into the transfer means. Accordingly, a solution that is adapted to the specific needs of a certain patient can be provided shortly before the actual coating of the medical implant.

Particularly advantageous methods are characterized in that the liquid is applied to the medical implant surface to be coated on all sides using a ring-shaped transfer means. This accounts for the specific geometry of many medical implants, in particular of articular prostheses.

In order to prevent contamination of the surroundings by the liquid, a preferred embodiment of the present invention can provide the medical implant to be introduced into a container, in which the transfer means is situated, before contacting it with the transfer means, and to be pulled out of the container after transfer of the liquid to the medical implant.

Another improvement is attained in that a powder is applied to the wetted surface of the medical implant after transfer of the liquid to the medical implant, preferably in that the medical implant is immersed into a powder. The powder can comprise, for example, at least one pharmaceutically active substance or at least one bone growth-stimulating compound. A suitable powder can, for example, promote bone growth and thus improve the success of an implantation since the powder effects a more stable connection of the implant to the adjacent bone material to be formed.

A preferred embodiment of the present invention can also provide the medical implant is pushed through at least one membrane or at least one membrane is opened before contacting the medical implant with the elastically deformable transfer means, for example by pressing onto the elastically deformable transfer means and/or sweeping over the elastically deformable transfer means, immersing in the powder and/or pressing onto the powder, whereby the at least one membrane covers at least regions of the liquid and/or powder, preferably the at least one membrane seals the powder in the container. The membrane prevents contamination of the liquid and/or powder prior to its use. Puncturing the membrane ensures that the protective membrane is opened only shortly before its use. For this purpose, the membrane should be structured such that no shreds or other parts of the membrane can enter into the liquid or powder or adhere to the medical implant.

Another refinement of the method according to a preferred embodiment of the present invention can be to provide a powder that matches the treatment scenario.

A preferred embodiment of the present invention can also provide that an antibiotic or mixture of antibiotics matching the treatment scenario is introduced into the powder. These two measures allow for individual adaptation to the actual treatment scenario of the respective patient.

Particularly advantageous refinements of a preferred embodiment of the present invention are characterized in that the powder comprises calcium phosphate powder, particularly preferably a mixture of α- and β-calcium phosphate, as bone growth-promoting substance. A reduction of the possible risk of contaminating the surroundings and savings of the often expensive coating materials can be attained according to the invention in that part of the liquid and/or powder transferred is wiped off, in particular when the medical implant is pulled out of the container, preferably at a wiper designed for this purpose. This can prevent or at least reduce contamination of the surroundings, for example, in particular of an OR area, by the liquid and, if applicable, by the powder. This is advisable especially upon the use of antibiotics since it allows the development of resistant pathogens in the OR area to be prevented.

In order to render the coated region and the completeness of coating visible, the invention can provide that the liquid is made to be colored such that the coated region of the medical implant can be identified by color.

In this context, a preferred embodiment of the present invention can provide that the completeness of coating of the region to be coated is tested by means of said coloration.

A preferred embodiment of the present invention can also provide the implant to be coated to be contacted repeatedly with the elastically deformable transfer means, preferably to be pressed repeatedly against the elastically deformable transfer means and/or to be swept repeatedly over the elastically deformable transfer means.

A preferred embodiment of the present invention can also provide for the method to be repeated as often as required for complete coating of the medical implant surface to be coated to be attained. In particular in the context of coloration of the liquid and testing of the completeness of coating through said coloration, this is advantageous according to the invention in order to obtain a sufficiently coated medical implant.

Moreover, a preferred embodiment of the present invention can provide that at least 50% of the surface of the medical implant, preferably at least 80%, particularly preferably 90% of the surface of the medical implant, are being coated.

A particularly advantageous refinement of the method is characterized in that non-cemented hip endoprostheses, shoulder endoprostheses, elbow prostheses, marrow nails or osteosynthesis plates are used as medical implant.

With regard to the device, the objectives are met in that the device comprises an elastically deformable transfer means that comprises a liquid that contains at least one pharmaceutically active substance such that the liquid can be transferred to the medical implant when the transfer means is contacted with the medical implant surface to be coated, preferably when pressing against the transfer means and/or sweeping past the transfer means. The elastically deformable transfer means is preferably soaked with the liquid.

In this context, a preferred embodiment of the present invention can provide the transfer means to be arranged in a container comprising an opening for introducing and taking out the medical implant. The purpose of the container is to prevent inadvertent splashing of the liquid.

In this context, a preferred embodiment of the present invention can again provide the opening to be closed through a pull-off lid. This allows contamination of the content prior to the use of the device to be prevented.

A particularly advantageous refinement of a preferred embodiment of the present invention can provide the device to comprise a wiper that is preferably arranged in the region of the opening, in particular between the opening and the transfer means.

In this context, a preferred embodiment of the present invention can provide the wiper to be disc-shaped and to comprise at least one notch that connects the top and the bottom of the disc.

Alternatively, a preferred embodiment of the present invention can provide the wiper to be shaped like an envelope of cone or a hemispherical surface, whereby the tip of the cone or the hemisphere is oriented towards the transfer means and the cone or the hemisphere preferably contain at least one notch that connects the top and the bottom of the wiper. Through this means, any droplet or particles that might detach from the transfer means while pulling the implant out can travel only in such a manner that they hit the internal wall of the container and hit the bottom of the wiper and any contamination of the surroundings by liquid is thus prevented.

Particularly advantageous devices are characterized in that the transfer means comprises pores and in that the liquid is contained in the pores of the transfer means, preferably in the form of a solution and/or suspension.

Moreover, a preferred embodiment of the present invention can provide the transfer means to comprise at least one roller, at least one rotatable sphere and/or at least one sponge that can be used to transfer the liquid to the medical implant surface to be coated.

A particularly preferred refinement of a preferred embodiment of the present invention provides the pharmaceutically active substance to contain antibiotics and/or organic antiseptic agents in a manner such that the coating to be generated contains a pharmaceutically active dose.

Moreover, a preferred embodiment of the present invention can provide the device to comprise a vacuum connection that can be connected to a vacuum source and is preferably arranged between the wiper and the transfer means. This can ensure, in addition, through the aspiration of possible droplets of the liquid and/or suspension that no contamination of the surroundings by pharmaceutical agents occurs.

According to another refinement, a preferred embodiment of the present invention can provide the transfer means to be manufactured from a hydrophilic material and preferably at least one other part, in particular the container and/or the wiper, to be manufactured from a hydrophobic material. It is preferable to use aqueous solutions and/or suspensions of pharmaceutical agents for coating. Provided the transfer means is manufactured from a hydrophilic material, aqueous solutions and/or suspensions are preferably situated in the porous hydrophilic material, rather than on the hydrophobic surface of the container and of the wiper. This behavior allows coating devices pre-filled with aqueous solutions and/or suspensions to get by with even the least volumes of said aqueous solutions or suspensions and still allow for assured coating.

A preferred embodiment of the present invention can also provide for the wiper to be made of a biocompatible elastomer, thermoplastic material, a metal foil or composites that are manufactured from metal-elastomer combinations or metal-plastics combinations.

Another refinement of a preferred embodiment of the present invention provides the wiper as a ring that contains bristles that are arranged to be radial with respect to the centre of the container and, if applicable, can form a cone whose tip is arranged in the direction of the transfer means. The bristles can be made of plastic material, whereby the mechanical stability and anchoring of the bristles are sufficiently strong for said bristles to neither break off nor become detached.

A preferred embodiment of the present invention can also provide the wiper as rollers and/or spheres that are connected to the container through elastic connecting means.

Moreover, a preferred embodiment of the present invention can provide the transfer means to be porous and elastic and preferably to be formed from a porous hydrophilic plastic material.

In this context, a preferred embodiment of the present invention can provide the porous elastic transfer means to be an envelope of cone or planar disc or arced, whereby it is preferable that at least one notch connects the top of the transfer means to the bottom of the transfer means and, in the case of an envelope of cone, that the tip of the cone is arranged in the direction of the wiper. The implant can be introduced into the device through the at least one notch.

It is particularly advantageous in this context to have radial notches formed in the wiper. This enables the entire external circumference of the implants to be wiped off after coating is completed and thus to remove any excess quantities of the solution or suspension from the coated implant surface. Moreover, it enables to effectively prevent the release of droplets or particles of the liquid or suspension that might arise while pulling the implant out of the liquid. Contamination of the surroundings is thus largely prevented.

A preferred embodiment of the present invention can also provide the transfer means to be a ring that comprises bristles arranged radially with respect to the centre that are preferably provided to project perpendicular with respect to the internal wall of the container or at an acute angle with respect to the internal wall of the container in the direction of the wiper.

Moreover, a preferred embodiment of the present invention can provide the device to be filled by an aqueous or organic-aqueous or organic solution and/or a suspension of at least one pharmaceutical agent or to not contain a pharmaceutical agent initially.

A preferred embodiment of the present invention can also provide for the wiper to be made of a biocompatible elastomer, thermoplastic material and/or a metal foil or composites that are manufactured from metal-elastomer combinations or metal-plastic combinations.

According to the scope of a preferred embodiment of the present invention, β-tricalcium phosphate, α-tricalcium phosphate, calcium phosphate made amorphous, tetracalcium phosphate, octacalcium phosphate, hydroxylapatite, fluoroapatite, calcium sulfate hemihydrate, calcium sulfate dihydrate, anhydrous calcium sulfate, powdered antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof are used as powder. The powder can also contain complexing agents or salts that form poorly water-soluble complexes or salts with the pharmaceutical agents that are transferred from the wiper to the implant surface. The powder can thus contain, for example, teicoplanin that forms poorly water-soluble complexes with gentamicin or other cationic antibiotics. It is also feasible, for example, that the powder contains N-methylglucammonium salts of fatty acids or of alkyl sulfates, which can form poorly water-soluble fatty acid salts or alkyl sulfates of the antibiotics upon exposure to aqueous solutions of cationic antibiotics owing to a reciprocal salt exchange. This means enables the application of poorly water-soluble complexes or salts of pharmaceutical agents, in particular of antibiotics, onto the implant surface.

It is particularly advantageous to use reactive inorganic powders, such as calcium phosphate made amorphous, tetracalcium phosphate and calcium sulfate hemihydrate, which harden in the presence of water. It is thus feasible to form stable coatings. Hardening within just a few seconds can be achieved, for example when calcium sulfate hemihydrate is used as the powder, through the addition of small amounts of calcium sulfate dihydrate as a nucleation agent and ammonium sulfate, sodium sulfate or potassium sulfate as accelerator to the calcium sulfate hemihydrate. Moreover, the use of β-tricalcium phosphate, α-tricalcium phosphate, and tetracalcium phosphate, which harden within just a few seconds upon exposure to the influence of aqueous acids, in particular of aqueous solutions of malic acid, tartaric acid, and citric acid, is also advantageous.

A preferred embodiment of the present invention is based on the surprising finding that the use of transfer means enables a coating that can be applied during or shortly before a surgery. This allows the coatings to be adapted to the individual needs of the patients. Moreover, the use of the transfer means reduces the risk of splashing the liquid and contamination of the surroundings is thus prevented. This is important especially for use in an operating theatre.

Thus is provided a method according to a preferred embodiment of the present invention for rapid and simple coating of medical implants with pharmaceutical preparations under OR conditions. Moreover, many refinements according to a preferred embodiment of the present invention achieve that the release of droplets or splashes of agent in the OR area is largely prevented. The coating device is designed in particular for the inexpensive coating with pharmaceutical agents of non-cemented articular endoprostheses, non-cemented revision articular endoprostheses and osteosynthesis material.

Accordingly, rather than coating the medical implant much earlier during its manufacture, it can also be coated right before inserting it. This allows relatively short-acting coatings to be used as well. Moreover, even a layer that is still liquid can be used, which opens up new application fields and renders new active substances accessible.

The device can be pre-filled with a solution and/or a suspension of an agent such that the OR staff simply needs to open the device and can then proceed with coating the implant instantaneously. In this context, it is advantageous that the time expenditure for said coating is in the range of but a few seconds and valuable OR time can thus be saved.

Alternatively, it is feasible to provide a non-pre-filled device with one or more pharmaceutical agents right in the OR theatre through injection of a solution or suspension of an agent. In the case of the antibiotic coating, this enables suitable selection of an antibiotic or combination of antibiotics based on the existing resistance status and thus ensures that the coating matches the antibiotic sensitivity pattern.

It is also feasible to fill non-pre-filled devices with suitable solutions or suspensions of agents in the respective hospital pharmacy prior to a surgery such that the coating can be carried out during the surgery without any time delay.

It is particularly suitable in this context to use as pharmaceutically active substance at least one member of the group of pharmaceutical agents, such as, for example, antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

For initial antibiotic protection, it is sufficient to have sufficiently high concentration(s) of antibiotic or antibiotics at the implant surfaces for a period of 24 to 72 hours. Therefore, sufficient temporary local antibiotic protection of the medical implant can be attained even upon local introduction of simple water-soluble antibiotics.

The device can be provided as drug or as medical product.

A combination of the device according to a preferred embodiment of the present invention and a medical implant could be offered as well. The combination is formed by the device and the implant, whereby said combination has a minimal service life of 0.1 seconds. The combination arises during the coating process.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Exemplary embodiments of the invention shall be illustrated in the following on the basis of five schematic figures, though without limiting the scope of the invention. In the figures.

DETAILED DESCRIPTION OF THE INVENTION

Figure 1:
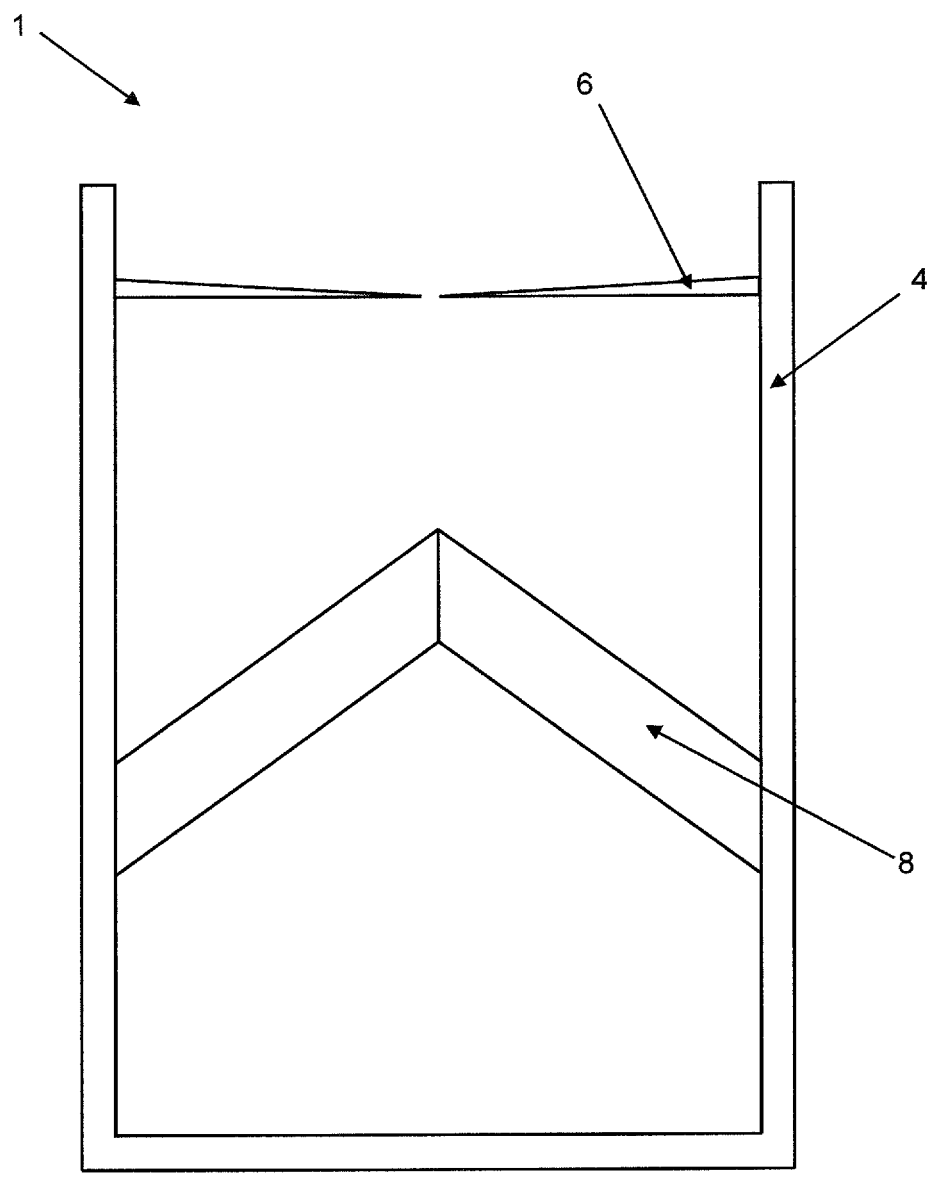
FIG. 1 is a schematic cross-sectional view of a transfer means in a container according to a preferred embodiment of the present invention.

Certain terminology is used in the following description for convenience only and is not limiting. The words "bottom" and "top" designate directions in the drawings to which reference is made. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIG. 1 shows a schematic cross-sectional view of a device 1 according to a preferred embodiment of the present invention. The device 1 includes a container 4 preferably in the form of a jar that is open on its top. The side walls of the container 4 are preferably cylindrical and of even thickness. A wiper 6 is preferably arranged on the inside of the container 4 in the region of the opening, just below the opening, and closes the opening nearly fully except for a circular opening in the middle.

The floor and side walls of the container 4 and the wiper 6 are preferably manufactured from a hydrophobic material or coated with a hydrophobic layer. Originating from the circular opening of the wiper 6, the wiper 6 is slitted or notched in eight directions.

The eight slits/notches (not shown) do not reach all the way to the side walls of the container 4 and are meant to enable the introduction of a medical implant through the wiper 6. The wiper 6 thus has eight flexible segments that wipe off the medical implant while pulling it out or while introducing or pulling it out, meaning that they sweep over the surface of the implant. The diameter of the circular opening of the wiper 6 is smaller than the cross-section of the medical implants to be introduced. This ensures that the wiper 6 sweeps over essentially the entire surface of the medical implant, in particular when it is being pulled out, and thus wipes it off A transfer means 8, in which slits are arranged as well, is arranged inside the container 4. The transfer means 8 is manufactured from a flexible porous material, such as a sponge. The transfer means 8 is saturated with an aqueous solution comprising an antibiotic. The material is hydrophilic. This ensures that it can be soaked with an aqueous liquid. Owing to the hydrophobic properties of the container 4 and wiper 6, the aqueous liquid is situated mainly in the transfer means 8.

The device 1 shown can be used to carry out a method according to a preferred embodiment of the present invention. The transfer means 8 is soaked with an aqueous solution that contains at least one pharmaceutically effective substance to be used to coat a medical implant. The transfer means 8 can be soaked with the liquid through a connection (not shown). Alternatively, the transfer means 8 can be filled using a syringe proceeding through the circular opening in the wiper 6 or through the wiper 6.

A medical implant (not shown) is pushed through the wiper 6 to meet the transfer means 8. Owing to the pressure exerted on the transfer means 8 through the medical implant, the medical implant not only pushes through the breaches designed for this purpose in the transfer means 8, but also the liquid contained in the transfer means 8 is pushed out of the transfer means 8 and applied to the surface of the medical implant.

Once the surface of the medical implant has been coated, the medical implant is pulled out of the container 4. The coated surface of the medical implant is pulled past the wiper 6 in the process. Any excess liquid is thus wiped off the surface of the medical implant and drips back onto the transfer means 8. The medical implant pulled out of the container 4 does not drip any longer then. Moreover, the inclination of the transfer means 8, which is provided as an envelope of cone and whose tip points in the direction of the wiper 6, prevents the liquid from splashing. These two measures allow the liquid to be prevented from contaminating the surroundings. The medical implant coated with the liquid is then ready for use in a surgery.

Figure 2:
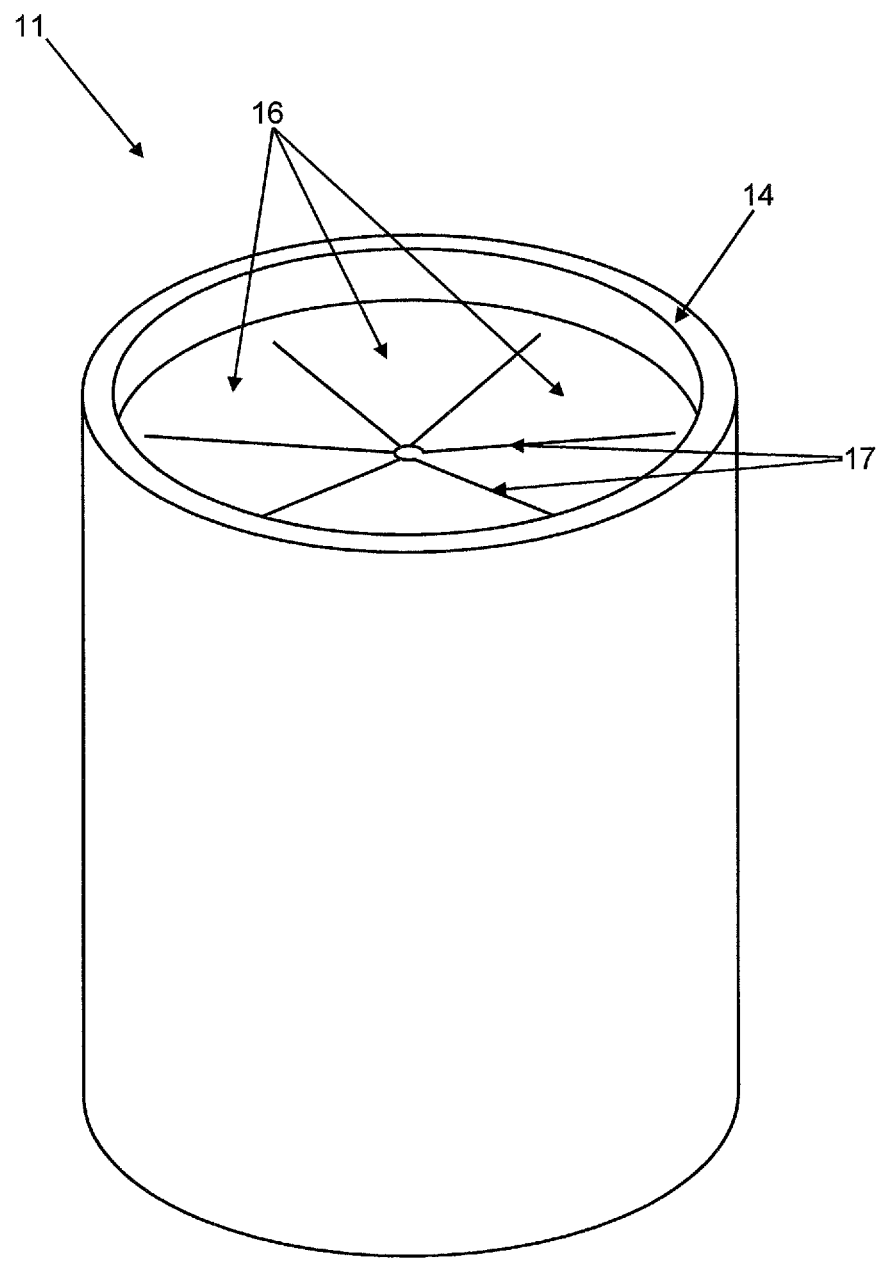
FIG. 2 is a schematic perspective view of a device according to a preferred embodiment of the present invention.

FIG. 2 shows a schematic perspective view of a second device 11 according to a preferred embodiment of the present invention for a method according to a preferred embodiment of the present invention. The device 11 includes a container 14 and a wiper 16 that completely closes the container 14 on its top. The flexible wiper 16 has six slits 17 or notches 17 that connect the top of the wiper 16 to the bottom of the wiper 16 facing the inside of the container 14 such that a medical implant (not shown) can be introduced into the inside of the container 14 through the wiper 16 along the slits 17 which are folded down in this situation.

On the inside of the container 14, there is a transfer means (not shown) situated that is made up of rotatable rollers on the surface of which a liquid layer is provided that can be used to coat the medical implant. A liquid reservoir re-supplies liquid to the rollers. When a medical implant is pushed through the wiper 16 into the inside of the container 14, the rollers of the transfer means transfer the liquid to the surface of the medical implant and thus coat the medical implant.

The wiper 16 ensures that excess liquid is wiped off the surface of the medical implant.

Examples of the production of a liquid for a method according to the invention and another example of a device according to the invention are illustrated in the following.

Example 1

Production of a Coating Solution Containing Gentamicin Sulfate

A total of 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed. A coating solution containing gentamicin sulfate as liquid for coating a medical implant was thus obtained.

Example 2

Production of a Coating Solution Containing the Two-Component Combination of Gentamicin Sulfate and Clindamycin Hydrochloride A total of 12.0 g gentamicin sulfate (Fujian Fukang Ltd.) were mixed with 4.0 g clindamycin hydrochloride (Sigma-Aldrich), and 4.0 ml pyrogen-free sterile water at room temperature. After stirring with a magnetic stirrer for 24 hours at room temperature, an oily-viscous yellowish solution had formed.

Example 3

Production of a Coating Solution Containing the Three-Component Combination of Gentamicin Sulfate, Clindamycin Hydrochloride, and Vancomycin Hydrochloride A total of 4.0 g gentamicin sulfate (Fujian Fukang Ltd.), 4.0 g clindamycin hydrochloride (Sigma-Aldrich), and 4.0 g vancomycin hydrochloride (Sigma-Aldrich) were mixed with 8.0 ml pyrogen-free sterile water at room temperature. After stirring with a magnetic stirrer for 24 hours at room temperature, a viscous yellowish solution had formed.

Example 4

Production of a Coated Implant

Conventional 10 ml plastic syringes were used to draw up 5 ml each of the coating solutions of the examples specified above. Then the filled plastic syringes were used to inject 4 ml of the corresponding agent solution onto a porous transfer means of a device according to the invention. The agent solution was thus soaked up through the porous transfer means.

Subsequently, customary Zweymüller hip prostheses were briefly dipped into a pre-filled device according to a preferred embodiment of the present invention until just before the end of the stem and then pulled out instantaneously. The Zweymüller hip endoprostheses are thus furnished with a viscous film of the agent solution at the surface of the stem.

The features of a preferred embodiment of the present invention disclosed in the preceding description and in the claims, figures, and exemplary embodiments, can be essential for the implementation of the various embodiments of the invention both alone and in any combination.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for coating at least regions of a medical implant, the device comprising:
   a container including an opening through which the medical implant is introduced and pulled out;
   a wiper arranged in a region of the opening;
   an elastically deformable transfer means arranged in the container, the elastically deformable transfer means being made of a hydrophilic material and including pores; and
   a liquid containing at least one pharmaceutically active substance, the liquid being contained in the pores of the elastically deformable transfer means in the form of a solution or suspension, the elastically deformable transfer means being configured to transfer the liquid to the medical implant upon contact with a surface of the medical implant
      wherein a gap exists between the wiper and the elastically deformable transfer means.

2. The device according to claim 1, wherein the opening is closed by a pull-off lid.

3. The device according to claim 1, wherein the wiper is arranged between the opening and the elastically deformable transfer means.

4. The device according to claim 3, wherein the wiper is in the form of a disc and comprises at least one notch that connects a top and a bottom of the disc.

5. The device according to claim 3, wherein the wiper is shaped like an envelope of cone or a hemispherical surface, and wherein a tip of the cone or the hemisphere is oriented toward the elastically deformable transfer means and the envelope of cone or the hemisphere contains at least one notch that connects a top and a bottom of the wiper.

6. The device according to claim 1, wherein the elastically deformable transfer means comprises at least one roller, at least one rotatable sphere or at least one sponge configured to transfer the liquid to the surface of the medical implant.

7. The device according to claim 1, wherein the at least one pharmaceutically active substance contains antibiotics or organic antiseptic agents such that a coating to be generated contains a pharmaceutically active dose.

8. The device according to claim 1, wherein at least one of the container and the wiper is manufactured from a hydrophobic material.

* * * * *